(12) United States Patent
Stubbs et al.

(10) Patent No.: US 8,216,189 B2
(45) Date of Patent: *Jul. 10, 2012

(54) CONTINUOUS GAS FLOW TROCAR ASSEMBLY

(75) Inventors: Jack B. Stubbs, Waynesville, OH (US); Ronald J. Thompson, Ft. Thomas, KY (US); George A. J. Hartman, Waynesville, OH (US); Donald N. Halgren, Manchester, MA (US); Michael J. Campbell, Louisville, KY (US)

(73) Assignee: SurgiQuest, Inc., Milford, CT (US)

( * ) Notice: Subject to any disclaimer, the term of this patent is extended or adjusted under 35 U.S.C. 154(b) by 1706 days.

This patent is subject to a terminal disclaimer.

(21) Appl. No.: 11/517,750

(22) Filed: Sep. 8, 2006

(65) Prior Publication Data
US 2007/0088276 A1    Apr. 19, 2007

Related U.S. Application Data

(62) Division of application No. 10/441,149, filed on May 17, 2003, now Pat. No. 7,182,752.

(60) Provisional application No. 60/461,149, filed on Apr. 8, 2003.

(51) Int. Cl.
*A61M 5/178* (2006.01)

(52) U.S. Cl. ... 604/167.01; 604/23; 604/26; 604/164.01

(58) Field of Classification Search ............... 604/23–26, 604/45, 506, 104, 164.01, 164.02, 164.03, 604/93.01, 158, 164.06, 164.07, 264, 164.09, 604/164.11, 167.01; 606/167, 185
See application file for complete search history.

(56) References Cited

U.S. PATENT DOCUMENTS

| | | | |
|---|---|---|---|
| 4,184,510 A | | 1/1980 | Murry et al. |
| 4,265,572 A | * | 5/1981 | Bourdois et al. ............... 406/114 |
| 4,535,773 A | | 8/1985 | Yoon |
| 4,735,603 A | | 4/1988 | Goodson et al. |
| 4,792,335 A | | 12/1988 | Goosen et al. |
| 4,869,717 A | | 9/1989 | Adair |
| 5,013,294 A | | 5/1991 | Baier |
| 5,190,068 A | | 3/1993 | Philbin |

(Continued)

FOREIGN PATENT DOCUMENTS

DE    195 23 685 A1    1/1997
(Continued)

OTHER PUBLICATIONS

International Search Report for related PCT application (PCT/US2006/045961).

(Continued)

*Primary Examiner* — Kevin C Sirmons
*Assistant Examiner* — Laura Schell
(74) *Attorney, Agent, or Firm* — Scott D. Wofsy; Edwards Wildman Palmer LLP

(57) ABSTRACT

A trocar assembly for providing a pressurized insufflation fluid into a patient cavity and for providing sealable access to the patient cavity by a surgical instrument. The assembly comprises an inner tubular member having a proximal end and a distal end. An outer tubular member is disposed about the inner tubular member, the outer tubular member having a proximal end and a distal end. The distal end of the inner tubular member and the distal end of the outer tubular member define a trocar seal nozzle arranged therebetween.

26 Claims, 9 Drawing Sheets

U.S. PATENT DOCUMENTS

| | | | |
|---|---|---|---|
| 5,199,944 A | 4/1993 | Cosmescu | |
| 5,203,767 A | 4/1993 | Cloyd | |
| 5,284,473 A | 2/1994 | Calabria | |
| 5,300,047 A | 4/1994 | Beurrier | |
| 5,312,351 A | 5/1994 | Gerrone | |
| 5,328,458 A | 7/1994 | Sekino et al. | |
| 5,545,150 A | 8/1996 | Danks et al. | |
| 5,800,381 A | 9/1998 | Ognier | |
| 5,849,005 A | 12/1998 | Garrison et al. | |
| 5,916,198 A | 6/1999 | Dillow | |
| 6,042,573 A | 3/2000 | Lucey | |
| 6,162,196 A | 12/2000 | Hart et al. | |
| 6,217,555 B1 | 4/2001 | Hart et al. | |
| 6,228,058 B1 | 5/2001 | Dennis et al. | |
| 6,253,766 B1 | 7/2001 | Niles et al. | |
| 6,299,592 B1 | 10/2001 | Zander | |
| 6,309,382 B1 | 10/2001 | Garrison et al. | |
| 6,482,181 B1 | 11/2002 | Racenet et al. | |
| 6,497,687 B1 | 12/2002 | Blanco | |
| 6,508,859 B1 | 1/2003 | Zia et al. | |
| 6,544,210 B1 | 4/2003 | Trudel et al. | |
| 6,579,270 B2 * | 6/2003 | Sussman et al. | 604/275 |
| 6,645,197 B2 | 11/2003 | Garrison et al. | |
| 6,685,665 B2 | 2/2004 | Booth et al. | |
| 6,905,489 B2 * | 6/2005 | Mantell et al. | 604/506 |
| 6,942,671 B1 | 9/2005 | Smith | |
| 7,182,752 B2 * | 2/2007 | Stubbs et al. | 604/164.01 |
| 7,285,112 B2 * | 10/2007 | Stubbs et al. | 604/167.01 |
| 7,297,141 B2 | 11/2007 | Kathrani et al. | |
| 7,338,473 B2 * | 3/2008 | Campbell et al. | 604/167.01 |
| 7,563,250 B2 * | 7/2009 | Wenchell | 604/167.01 |
| 7,854,724 B2 * | 12/2010 | Stearns et al. | 604/167.01 |
| 2002/0120226 A1 | 8/2002 | Beck | |
| 2002/0128603 A1 | 9/2002 | Booth et al. | |
| 2002/0161387 A1 | 10/2002 | Blanco | |
| 2003/0040711 A1 | 2/2003 | Racenet et al. | |
| 2003/0045834 A1 | 3/2003 | Wing et al. | |
| 2004/0199121 A1 | 10/2004 | Wenchell et al. | |
| 2005/0010164 A1 | 1/2005 | Mantell | |
| 2005/0015043 A1 | 1/2005 | Stubbs et al. | |
| 2006/0079925 A1 | 4/2006 | Kerr | |

FOREIGN PATENT DOCUMENTS

| | | |
|---|---|---|
| EP | 0 323 018 B1 | 6/1993 |
| EP | 1 188 415 A | 3/2002 |
| WO | WO 96/01132 A | 1/1996 |
| WO | WO 00/37134 | 6/2000 |
| WO | WO 01/91653 A | 12/2001 |
| WO | WO 02/33108 A2 | 4/2002 |

OTHER PUBLICATIONS

"Infant Flow System" from www.eme-med.co.uk.
"Air Jets and Nozzles" from www.exair.com.

* cited by examiner

CONTINUOUS GAS FLOW TROCAR ASSEMBLY

CROSS-REFERENCE TO RELATED APPLICATIONS

The subject application is a divisional of U.S. patent application Ser. No. 10/441,149, filed May 17, 2003, now U.S. Pat. No. 7,182,752, which claims the benefit of priority to U.S. Provisional Application Ser. No. 60/461,149, filed Apr. 8, 2003. Each of the foregoing applications is expressly incorporated herein by reference.

BACKGROUND OF THE INVENTION

1. Field of the Invention

The present invention relates to medical devices and more particularly to access devices and particularly their seal arrangements and closure mechanisms applicable to such medical devices.

2. Prior Art

Laparoscopic surgery is now standard procedure in hospitals today. Abdominal operations are being performed with narrow elongated instruments inserted through small incisions into interior portions of the body. Such laparoscopic procedures are now considered the treatment of choice for operations such as the removal of the gall bladder, spleen, adrenal glands, uterus and ovaries. Such laparoscopic procedures are accomplished via access through a device typically known as a trocar which facilitates the introduction of laparoscopic instruments into the abdomen of the body. The introductions of these instruments typically are done in regions which include a fluid under pressure. In the abdomen, this fluid may be a gas such as insufflation gas. It is desirable to provide for the introduction of a surgical instrument into the body cavity without permitting the reduction or loss of the operative pneumoperitoneum.

During typical laparoscopic procedures, the surgeon makes three to four small incisions, usually no larger than about twelve millimeters. These facial incisions are made with the trocar devices. The trocar makes the incision and then provides a tubular access for other instruments to be inserted into the abdominal space. The trocar also provides a means to insufflate the abdominal cavity with a low pressure gas, typically carbon dioxide, so that the surgeon has an open interior space in which to work. The trocar must provide a means to maintain the internal gas pressure with some sort of a seal between the trocar and the medical instrument he is utilizing, and still allow those surgical devices to be inserted and withdrawn. Such surgical instruments introduced through the trocar tube and into the abdomen may include scissors, grasping instruments, occluding instruments, cauterizing units, cameras, light sources and other surgical instruments.

Currently, insufflation is performed by providing a regulated pressurized gas to the peritoneal cavity via the trocar cannula. This gas, typically carbon dioxide, is supplied to a connection on the side of the trocar tube by a flexible hose there attached. The medical instrument going through the trocar or innermost tube thereof, should be sealed relative to the trocar so that insufflation gas will not escape from the patient.

Sealing mechanisms are utilized within the trocar to prevent the escape of fluid. Such mechanisms said typically comprised an aperture or septum valve which has functioned to form a seal around the outer surface of the instrument positioned and moved within the trocar or access device. When the instrument is inserted, or is removed, the hole in the seal contracts to restrict outward gas flow. Such seals usually accept a range of instrument diameters and usually do not totally restrict outward gas flow when these instruments are retracted. Other types of valves and seals include flapper valves or trap type doors which are spring loaded. When a instrument penetrates the trocar tube access device the instrument pushes the door open. However when the instrument is retracted, such a trap door or valve may interfere with the removal of the instrument or any tissue being transported thereby.

Certain problems arise with the types of seals utilized in these trocar devices. Certain seals only work for a limited range of instrument diameters. Certain other seals inhibit the motion of the instrument as it is being inserted or as it is being withdrawn from the trocar. Typically the seals do not last through any procedures because they are subject to wear and tearing. Those prior art seals also may often interfere with the removal of the instrument and/or any tissue being withdraw from the patient utilizing that particular instrument.

It is an object of the present invention to overcome the disadvantages of the prior art.

It is a further object of the present invention to provide a seal which will work with a wide range of instrument sizes, shapes and diameters.

It is a further object of the present invention to provide a universal trocar seal for use without the seal interfering with or touching any instrument utilized therewith.

It is still yet a further object of the present invention to provide a seal which will eliminate any motion restriction for those instruments inserted therethrough, and permit improved tactile feedback to the surgeon.

It is yet a further object of the present invention to provide a seal which may be automatic in its function, as well as being controllable and adjustable, by or according to the needs of the attending surgeon.

It is a further object of the present invention to provide a path for exiting liquid and gas and a collection arrangement therefore, with a prevention of any splash therewith.

It is still yet a further object of the present invention to provide a seal which will not interfere with the removal of tissue from the interior of a body cavity as it moves through the trocar.

It is still yet a further object of the present invention to allow instruments with an irregular outside surface configuration to still maintain a seal with the trocar.

It is yet another object of the present invention to allow an instrument and a trailing suture to be utilized as in a surgical procedure such as a Nissen fundal placation.

It is yet a further object of the present invention to permit the use of two instruments with a combined OD less than the ID of the cannula wherein one instrument could be used for grasping and stabilizing tissue the other instrument used for cutting that stabilized tissue or cannulation (cholangiogram) of a ductal tissue without the loss of gas or the use of a further trocar.

BRIEF SUMMARY OF THE INVENTION

The present invention comprises a continuous gas flow trocar arrangement which provides a completely open aperture for the introduction of a surgical instrument and its access to the peritoneum without any physical contact between the innermost surface of the trocar assembly and the surgical instrument being introduced therewithin or withdrawn therefrom. The trocar assembly of the present invention comprises an elongated outer tubular member having a first or proximal end and a second or distal end. The assembly includes an internal tubular member, which may be identified as a cannula, having an open proximal end and an open distal most end. An annular seal is disposed between the outer tubular member and the outer walls of the inner tubular member at the proximal end of the assembly. An insufflation gas flow supply conduit is in fluid communication with the annular plenum chamber arranged between the outer surface of the inner tubular member and the inner surface of the outer tubular member. Pressurized gas is thus presented to the continuous gas flow trocar via the insufflation gas conduit. The insufflation gas flows through the annular chamber between the inner and outer tubular members and is discharged into the abdomen of the patient at the second or distal end and of the trocar assembly.

The distal end of the trocar assembly defines an annular array of fluid directing jets which direct the insufflation gas flow through the annular nozzle arrangement preferably as a cone shaped gas stream or wall of gas exiting those jets or nozzles. In this continuous gas flow trocar assembly, the force produced by the jet fluid is counterbalanced by the pressure inside the peritoneum of the patient. This balance is achieved when the abdomen pressure by the inflow of insufflation gas is reduced until the desired peritoneal pressure just balances the inlet air flow force. The inlet gas flow will maintain the correct insufflation pressure within the patient's abdomen and will automatically adjust to allow laparoscopic medical instruments to be passed through the inner tubular member into the peritoneum and to be retrieved from the abdomen through the inner tubular member of the trocar assembly. Outflow of pressurized fluid is effected between the medical instrument within the inner tubular member and the inner walls of the inner tubular member and exiting out the access port at the proximal end of the trocar assembly. In the event that the instrument or instruments inserted through the trocar completely or nearly completely fills the inner tubular trocar member, the gas inflow is reduced to zero to maintain the desired, controlled, peritoneum pressure.

The medical instrument accessing the peritoneum through the inner tubular member of the trocar assembly and into the patient merely passes through the gaseous fluid wall created by the annular nozzles at the distal most end of the trocar assembly. Manipulation of that medical instrument is not interfered with nor is removal of any tissue through that inner tubular member hindered in any way by any trap door or overlapping seal arrangement typical of the prior art. The cannula or inner tubular member may be movable relative to the outer tubular member of the trocar assembly to permit changing of the flow of gases through the annular nozzle arranged within the distal end of the trocar assembly.

The invention thus comprises a trocar assembly for providing a pressurized insufflation fluid into a patient cavity and sealable access to the patient cavity by a surgical instrument, comprising: an inner tubular member having a proximal end and a distal end; an outer tubular member disposed about the inner tubular member, the outer tubular member having a proximal end and a distal end, the distal end of the inner tubular member and the distal end of the outer tubular member defining a trocar the nozzle arranged therebetween. The trocar seal nozzle arrangement introduces a wall of fluid material delivered between the distal end of the inner tubular member and the distal end of the outer tubular member. The trocar seal nozzle is preferably of arcuate configuration to conform to the tubular members. The inner tubular member preferably comprises a fluid return channel for insufflation fluid returned from the patient. The trocar seal nozzle comprises a pressurized fluid seal for penetration by a surgical instrument during a surgical procedure upon the patient. At least one of the tubular members has a pressure sensor arranged with a fluid pressure source to control fluid introduction into the patient. The pressurized fluid seal preferably comprises a wall of pressurized air. The wall of pressurized air is preferably of generally conical shape. A regulatable pressurized source is preferably in communication with the outer tubular member. The trocar seal nozzle may be adjustable. The inner tubular member may be rotatably adjustable with respect to the outer tubular member. The inner tubular member is preferably longitudinally adjustable with respect to the outer tubular member. The inner tubular member and the outer tubular member preferably have an annular space therebetween defining a plenum chamber for introduction of pressurized fluid from a pressurized fluid source in communication with the plenum chamber to a fluid discharge nozzle at the distal end of the trocar assembly to create a wall of pressurized fluid for sealing the trocar assembly. A flexible sleeve may be attached to the proximal end of the inner tubular member, the sleeve being arranged for receipt of a surgeon's forearm during manipulation of a surgical instrument through the trocar assembly and within the patient. The insufflation fluid comprises an instrument seal for the assembly.

The invention also may comprise a method for providing a pressurized insufflation fluid into a patient cavity and for providing sealable access to the patient cavity during a procedure with a surgical instrument, comprising: placing an inner tubular member having a proximal end and a distal end into an outer tubular member, the outer tubular member having a proximal end and a distal end, the distal end of the inner tubular member and the distal end of the outer tubular member defining a trocar seal nozzle arranged therebetween; forming an arcuate opening between the distal ends of the inner tubular member and the outer tubular member to comprise the nozzle; introducing a pressurized fluid into the outer tubular member; and discharging the pressurized fluid out of the nozzle at the distal end of the tubular members to form a wall of pressurized fluid to seal the trocar assembly during any surgical procedure performed therewith. The method may include: introducing a surgical instrument into the inner tubular member; extending the surgical instrument through the wall of pressurized fluid and into the cavity of the patient for surgical use therewithin; controlling the pressure, temperature and/or content of the pressurized fluid introduced through the nozzle and into the patient by a fluid control and fluid sensor feedback arrangement in communication with the fluid introduced into the patient; placing a plurality of spacers between the inner tubular member and the outer tubular member to maintain alignment therebetween. The surgical instrument introduced into the patient through the inner tubular member of the trocar assembly may comprise a catheter. The surgical instrument introduced into the patient through the inner tubular member may comprise a pair of scissors. The method may include removing a tissue sample from the patient by retraction of the sample through the wall of pressurized fluid at the distal end of the trocar assembly; changing the nozzle configuration by adjustment of the inner tubular member with respect to the outer tubular member; rotating the inner tubular member with respect to the outer tubular member to effect the changing of the nozzle configuration. The surgical procedure may comprise tying a suture within the patient. The method may include attaching a flexible sleeve to the proximal end of the inner tubular member for enclosed receipt of a surgeon's forearm.

The invention may include a method of sealing a trocar assembly within a cavity of a patient during a surgical procedure by an instrument within that cavity of the patient, comprising: introducing a pressurized air through a plenum in the trocar assembly to form a wall of air within the cavity of the patient to seal the cavity from excessive loss of air pressure within the cavity of the patient; piercing the wall of air by the instrument during the surgical procedure; maintaining a generally constant pressure within the cavity of the patient by supplying a constant flow of pressurized air through the plenum in the trocar assembly and into the cavity of the patient; manipulating the medical instrument with respect to the trocar assembly in the absence of interference by the trocar assembly with the instrument.

The invention may also include a surgical method including the steps of piercing the wall of air by the instrument during the surgical procedure; maintaining a generally constant pressure within the cavity of the patient by supplying a constant flow of pressurized air through the plenum in the trocar assembly and into the cavity of the patient; manipulating the medical instrument with respect to the trocar assembly in the absence of interference by the trocar assembly with the instrument, wherein a spiral groove may be arranged on an inner surface of an inner tubular member of the assembly; arranging a duckbill type valve at a proximal location of the inner tubular member to minimize splashing of exiting gas and liquid threat;

The invention may also comprise a trocar assembly for providing a pressurized insufflation fluid into a patient cavity and sealable access to the patient cavity concomitantly using one or more surgical instruments simultaneously in the patient, comprising: an inner tubular member having a proximal end and a distal end; an outer tubular member disposed about the inner tubular member, the outer tubular member having a proximal end and a distal end, the distal end of the inner tubular member and the distal end of the outer tubular member defining a trocar fluid seal nozzle arranged therebetween wherein a controlled pressurized fluid is supplied between the outer tubular member and the inner tubular member at or near a proximal end thereof for introduction into a patient through the generally annular nozzle at a distal end of the trocar assembly. The one or more surgical instruments may be comprised of a tissue grasping instrument and a tissue cutting instrument.

The invention may also comprise a method of surgically operating upon a patient, comprising one or more of the steps of: inserting a hollow, tubular trocar assembly through an abdominal opening in the patient; introducing a wall of pressurized fluid into the patient preferably via a generally annular nozzle arranged at a distal end of the trocar assembly; introducing at least one surgical instrument through the hollow tubular trocar assembly and into the patient through the wall of fluid; arranging a flexible arm receiving sleeve at a proximal end of the trocar assembly, the sleeve receiving a forearm of an operating surgeon therethrough. The method may include the steps of: adjusting a dimension of the annular nozzle to effect a change of fluid flow through; arranging a spiral groove on an inner surface of the inner tubular member of the trocar assembly to effect fluid flow exiting from the trocar assembly inserted in the patient; separating the fluid flow exiting from the trocar assembly into a gas, a liquid and/or a particle collection for evaluation of those components.

The trocar assembly may be preferably comprised of an inner tubular member and an outer tubular member generally concentric therewith. The pressurized fluid preferably comprises a gaseous substance. The inner tubular member preferably has an inner surface which has an array of spiral groove arranges therein to permit fluid and particle separation thereby upon exiting of the pressurized fluid max through said trocar assembly. An annular collection reservoir is preferably arranged at a proximal end of an innermost tubular member of the trocar assembly. The trocar assembly preferably includes a duckbill valve at a proximal end of the trocar assembly at an inner tubular member therewithin, for further sealing of a surgical instrument therethrough. The generally annular nozzle is in fluid communication with a plenum chamber arranged between an inner tubular member and an outer tubular member of the trocar assembly. The generally annular nozzle arranged at the distal end of the trocar assembly preferably has a plurality of guide vanes spaced therearound.

BRIEF DESCRIPTION OF THE DRAWINGS

The objects and advantages of the present invention will become more apparent when viewed in conjunction with the following drawings in which.

DETAILED DESCRIPTION OF THE PREFERRED EMBODIMENTS

Figure 1:
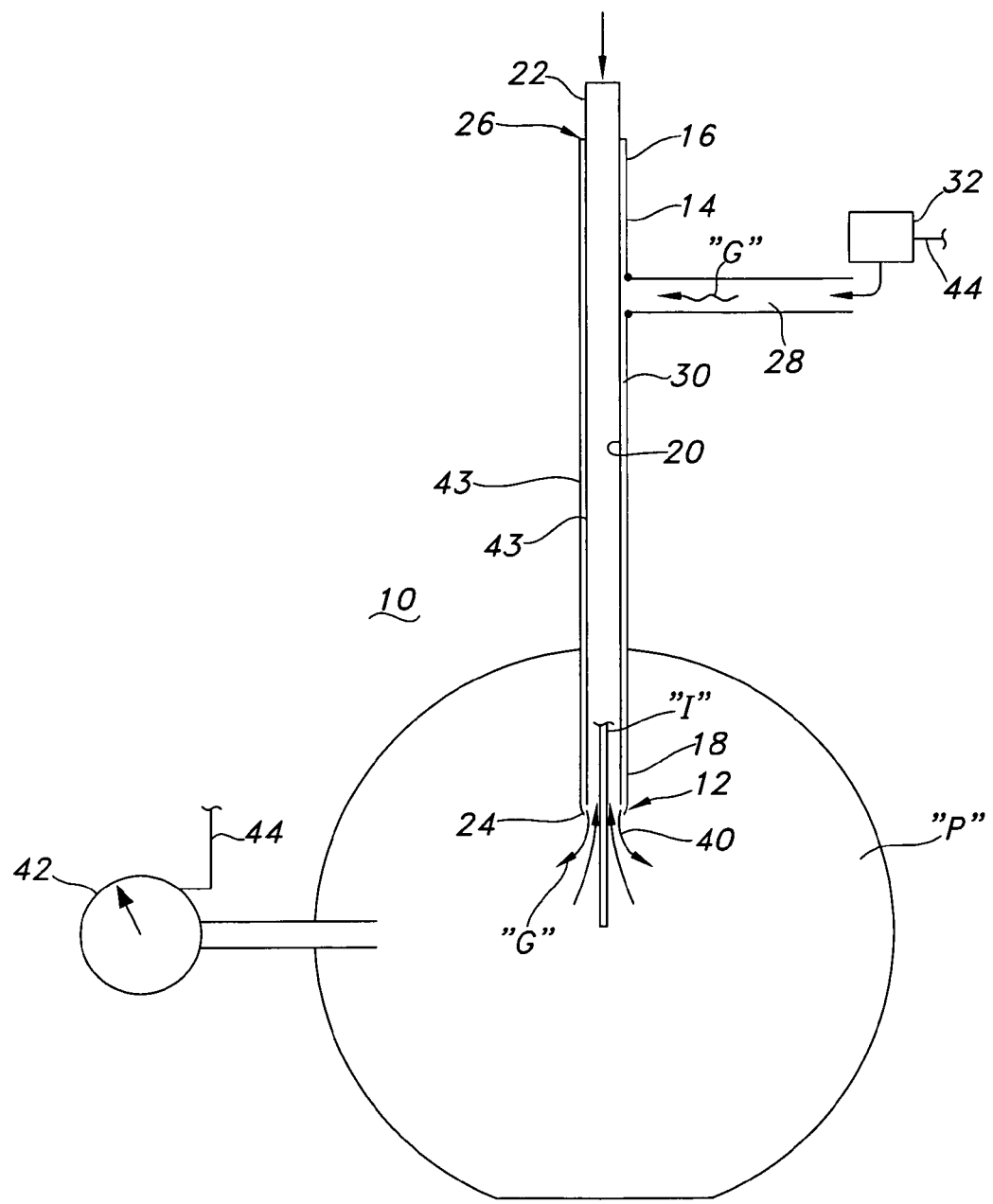
FIG. 1 is a schematic representation of a trocar assembly utilized within the exemplary abdominal cavity of a patient.

Referring now to the drawings in detail, and particularly to FIG. 1, there is shown the present invention which comprises a continuous gas flow trocar assembly 10 which provides a completely open aperture 12 for the introduction of a surgical instrument "I" and its access to the peritoneum "P" without any physical contact between the innermost surface of the trocar assembly 10 and the surgical instrument "I" being introduced therewithin or withdrawn therefrom. Use of the trocar assembly 10 would also include the use of an obturator (not shown for clarity) to pierce the patient's abdomen to permit the access into the patient via the trocar assembly 10. The trocar assembly 10 of the present invention comprises an elongated outer tubular member (cannula) 14 having a first or proximal end 16 and a second or distal end 18. The assembly 10 includes an internal tubular member 20, having an open proximal end 22 and an open distalmost end 24, the internal tubular member 20 defining an innermost instrument introduction channel 21. The open proximal end 22 also comprises an access port as described herebelow. An annular seal 26 is disposed between the outer tubular member 14 and the outer walls of the inner tubular member 20 at the proximal end of the trocar assembly 10, as represented in FIG. 1.

An insufflation fluid/gas flow supply conduit 28 is in fluid communication with the annular plenum chamber 30 arranged between the outer surface of the inner tubular member 20 and the inner surface of the outer tubular member 14. Pressurized fluid/gas "G", which may be tinted, heated, chilled, humidified, de-humidified or treated with a medicament, is thus presented to the plenum chamber 30 of the continuous gas flow trocar assembly 10 via the insufflation gas conduit 28 from a regulatably controllably, pressurized source 32 for introduction into the peritoneum "P" of a patient. The insufflation fluid/gas "G" thus flows through the annular chamber 30 between the inner and outer tubular members 20 and 14 and is discharged into the peritoneum "P" of the patient through, in one preferred embodiment, a generally adjustable annular nozzle 36 arranged at the second or distal end 18 and of the trocar assembly 10.

Figure 2:
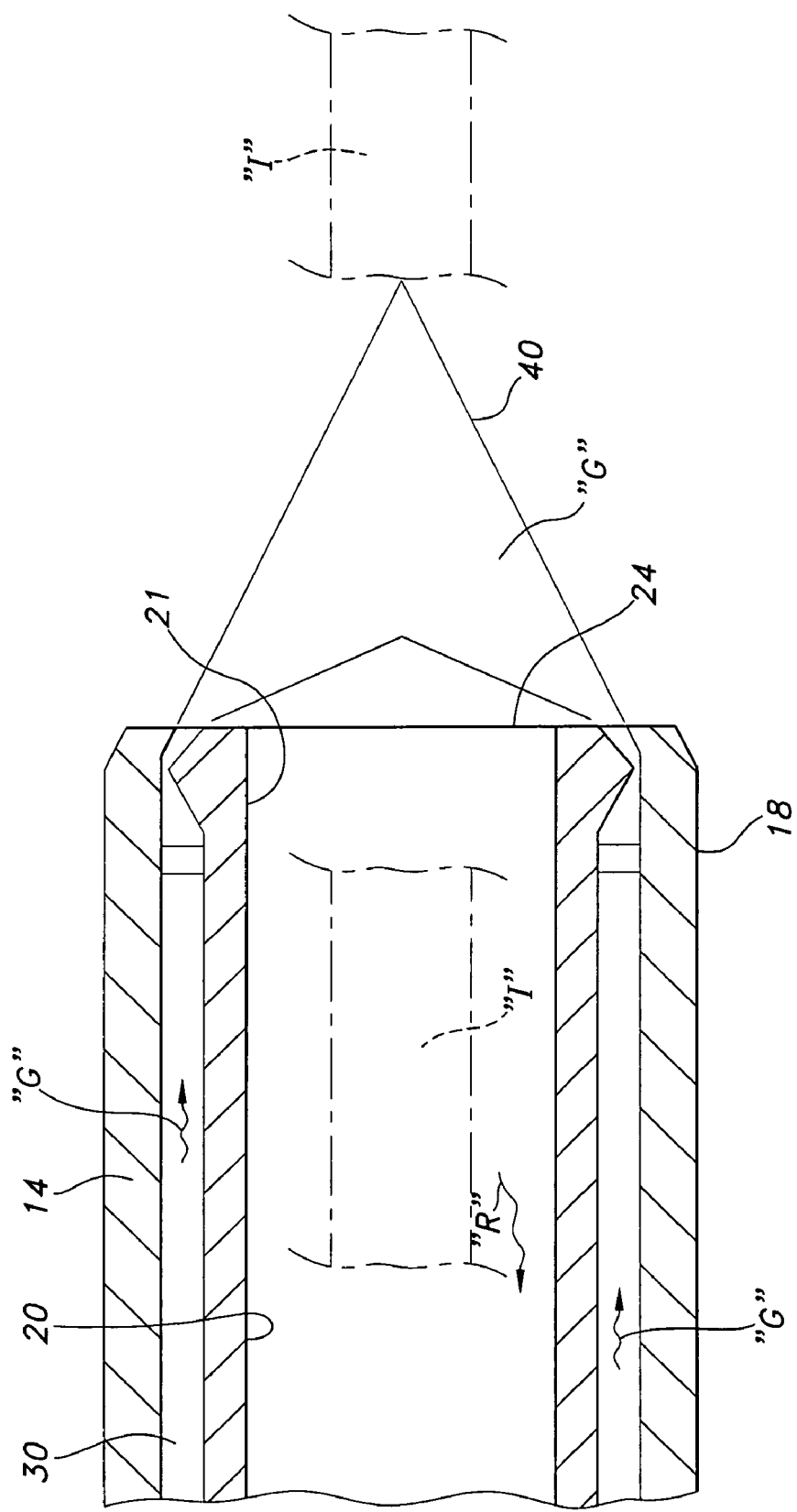
FIG. 2 is a side elevational view, in longitudinal section, of the distalmost end of a trocar assembly constructed according to the principles of the present invention.
Figure 3:
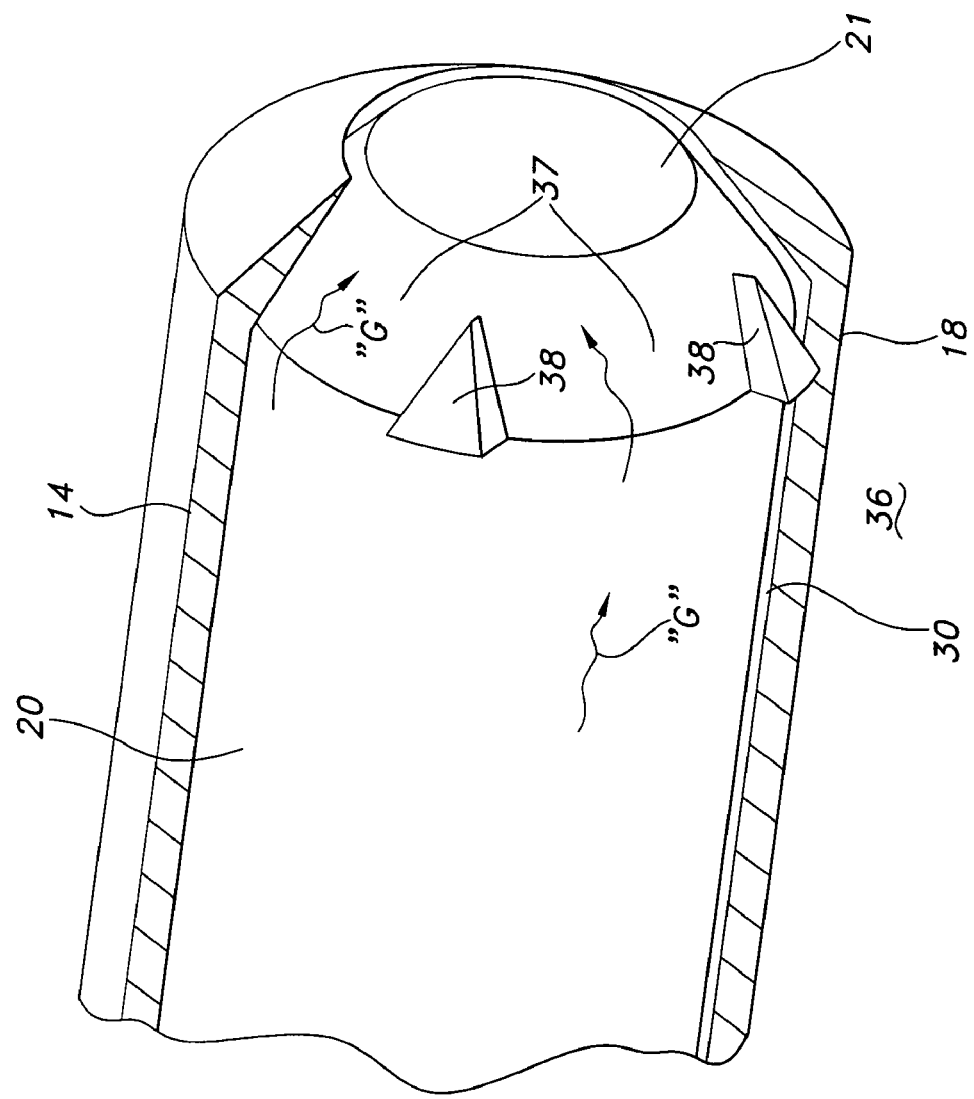
FIG. 3 is a perspective view with portions cut away, of the distalmost end of the trocar assembly of the present invention.

The distal end 18 of the trocar assembly 10 defines the annular fluid flow nozzle arrangement 36, as is more clearly represented in FIGS. 2 and 3. In one preferred embodiment of the nozzle arrangement 36, an array of radially outwardly extending fluid directing spacers, vanes or jets 38 are arranged to direct the insufflation/treatment fluid/gas "G" flowing therethrough, in a cylindrical stream in the annular plenum chamber 30 and through the annular nozzle arrangement 36 to discharge therefrom, as for example, in a cylindrically (preferably cone) shaped gas stream or wall of fluid or gas 40 exiting the annular arrangement of arcuate openings 37 between those jets or vanes 38.

In this continuous gas flow trocar assembly 10, the force produced by the jet fluid is counterbalanced by the pressure inside the peritoneum "P" of the patient as sensed by a pressure sensor 42, extending into the peritoneum "P", as represented in FIG. 1. The pressure sensor 42 is in proper communication with the computer controlled pressure source 32 by a communication line 44. This balance is achieved when the abdominal pressure by the inflow of insufflation fluid/gas "G" is reduced until the desired peritoneal pressure just balances the inlet air flow force as generated by the pressure source 32. The inlet fluid/gas "G" flow will maintain the correct insufflation pressure within the patient's abdomen and may be automatically controlled by computer means with the pressure source 32 so as to adjust to fluid/gas flow to allow laparoscopic medical instruments to be passed through the inner tubular member 20 into the peritoneum and to be retrieved from the abdomen through that inner tubular member 20 of the trocar assembly 10. In a further embodiment, a pressure sensor 43 may be arranged within the inner tubular member 20 or within the outer tubular member 14, or both, as represented in FIG. 1.

Outflow of returned pressurized fluid/gas "R" is effected between the medical instrument "I" within the inner tubular member 20 and the inner walls of the inner tubular member 20 and exiting out the access port 22 at the proximal end 16 of the trocar assembly 10, as represented by the letter "R" in FIG. 2.

The (those) medical instrument(s) "I" accessing the peritoneum through the inner tubular member 20 of the trocar assembly 10 and into the patient merely passes through the gaseous fluid wall 40 created by the pressurized fluid forced through the annular nozzle arrangement 36 at the distalmost end 18 of the trocar assembly 10. Manipulation of that (those) medical instrument(s) "I" is (are) not interfered with nor is removal of any tissue through that inner tubular member 20 hindered in any way by any trap door or overlapping seal arrangement typical of the prior art. The cannula or inner tubular member 20 may be movable relative to the outer tubular member 14 of the trocar assembly 10, as will be described more fully hereinbelow, to permit a slight changing of the flow of gases "G" through the annular nozzle 36 arranged within the distal end 18 of the trocar assembly 10.

Figure 4:
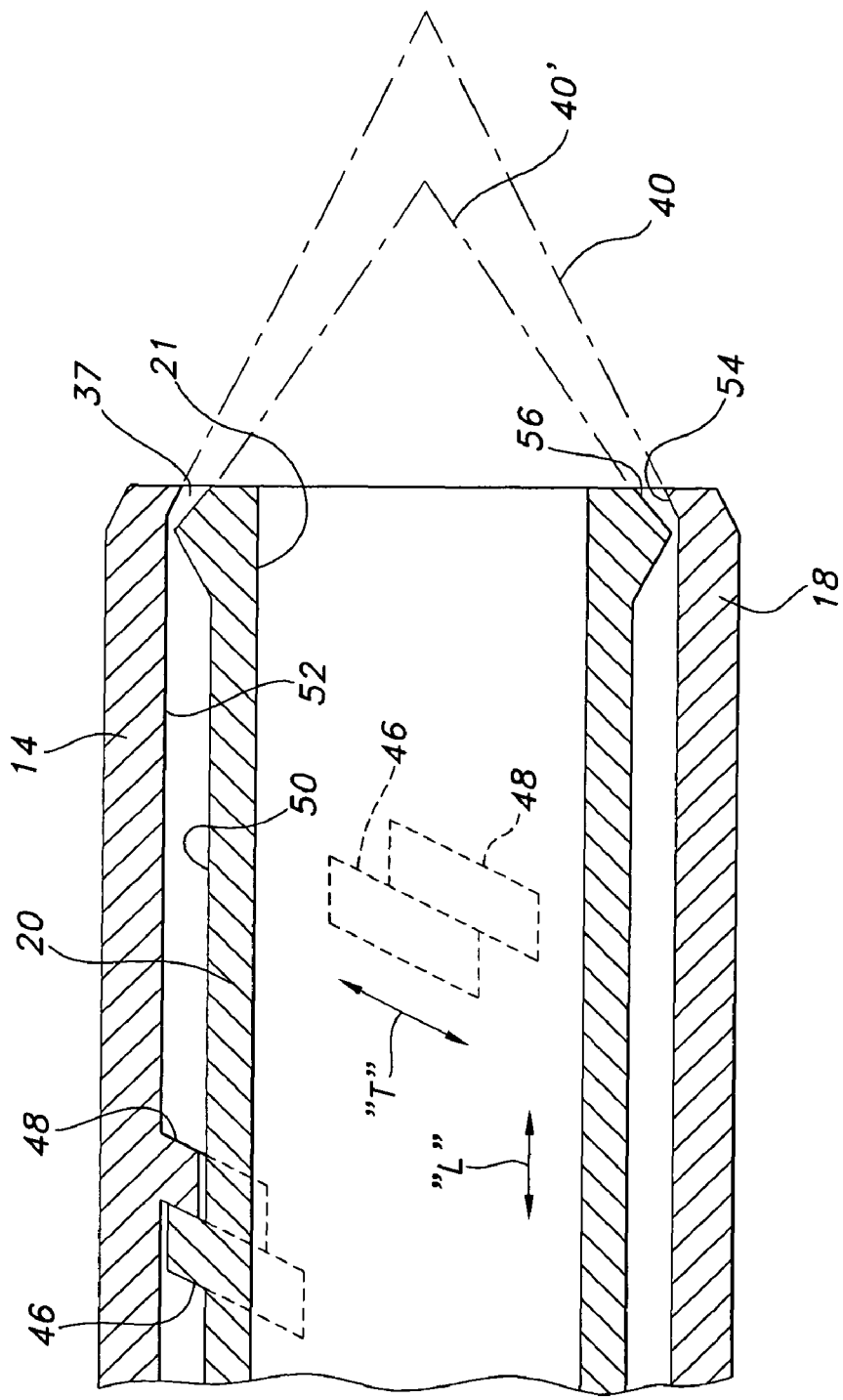
FIG. 4 is a side elevational view of the adjustability arrangement of the inner tubular member relative to the outer tubular member of the trocar assembly, to permit longitudinal movement and hence flow adjustment to device's downstream annular valve arrangement.

In a further preferred embodiment of the present invention, a plurality of short, spaced apart, slidably engaging arcuate screw threads 46 and 48 may be arranged on the outer surface 50 of the inner tubular member 20 and the inner surface 52 of the outer tubular member 14, respectively. Rotation of the inner tubular member 20 with respect to the outer tubular member 14 by the attending surgeon as indicated by the arrow "T", in FIG. 4, would in this embodiment, effect longitudinal adjustment between the inner tube 20 and the outer tube 14, as indicated by the arrow "L" for adjusting the nozzle 36. The adjustment is effected by effecting dimensional changes in the spacing between the surfaces 54 and 56 comprising the arcuate segments of the nozzle 36, which gap for such nozzle 36 may for example be about 0.006 inches. Such dimensional changes in the nozzle 36 would change the locus of the fluid/gas wall 40 developed at the distal end 18, of the trocar assembly 10, as represented in FIG. 4.

Figure 5A:
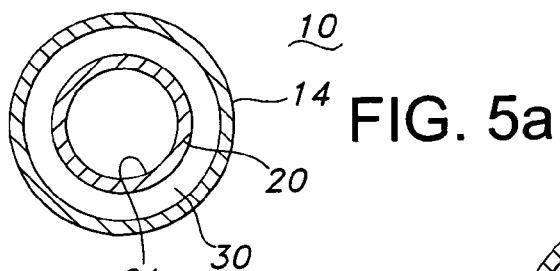
FIG. 5a through FIG. 5k represents a cross-sectional view of the inner and outer tubular members having various medical instruments being utilized therethrough.
Figure 5B:
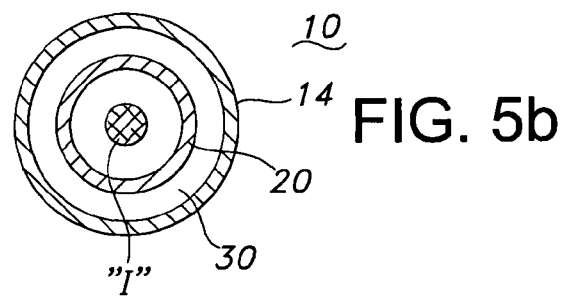
Figure 5C:
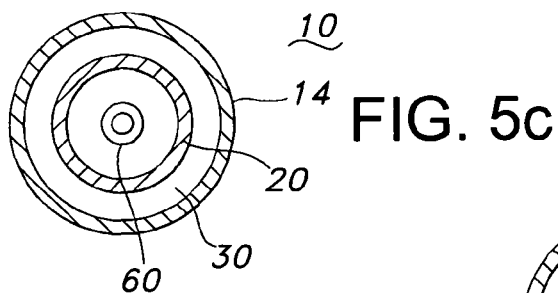

A sectional representation of the inner and outer tubular members 20 and 14 of the trocar assembly 10 are shown in FIGS. 5a through 5k. FIG. 5a discloses the inner tube 20 spaced apart and arranged within the outer sleeve or tube 14, the outer tube having for example, an outer diameter of about 7 mm., the inner tubular member 20 having an operating channel diameter of about 5 mm., the discharge return gas "R" passing proximally between the inner wall 21 of the inner tube 20 and the instrument "I". FIG. 5b represents the inner and outer tubular members 20 and 14, with an instrument "I" of less that 5 mm. operatively arranged therewithin. FIG. 5c represents the inner and outer tubular members 20 and 14 utilized with a flexible catheter 60, for example, a cholangiogram catheter.

Figure 5D:
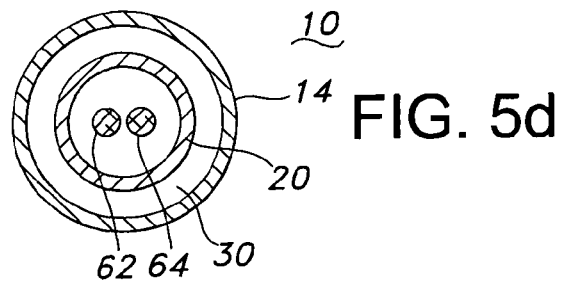
Figure 5E:
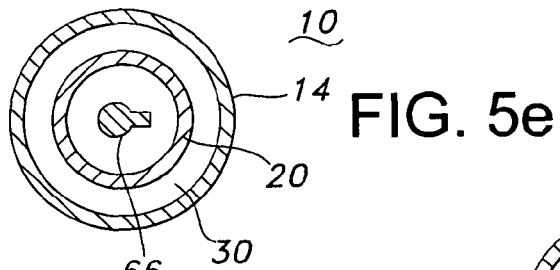
Figure 5F:
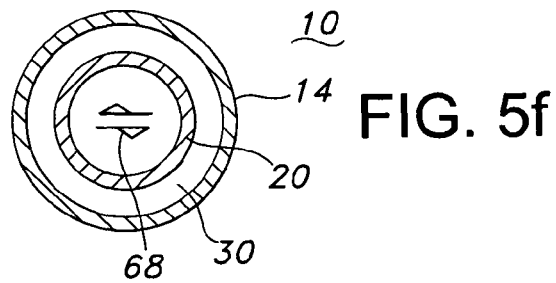
Figure 5G:
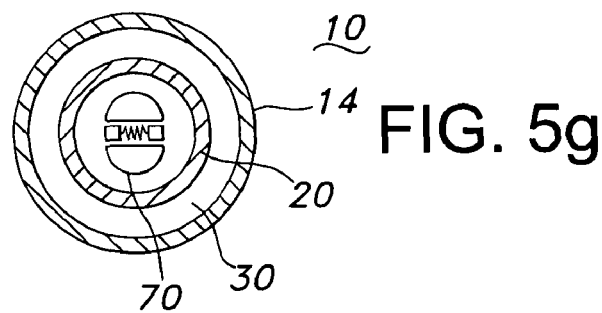
Figure 5H:
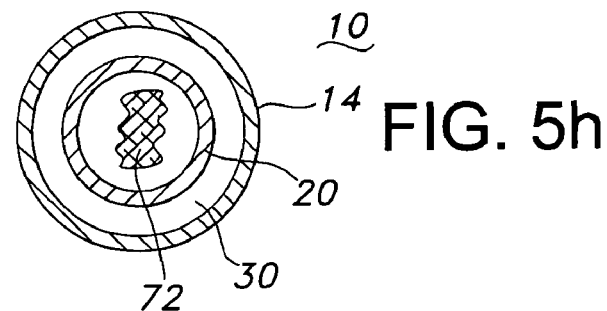
Figure 5I:
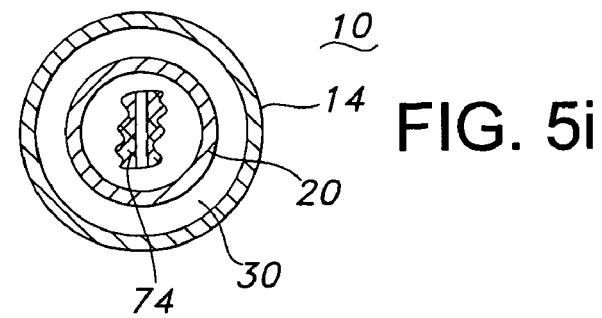
Figure 5J:
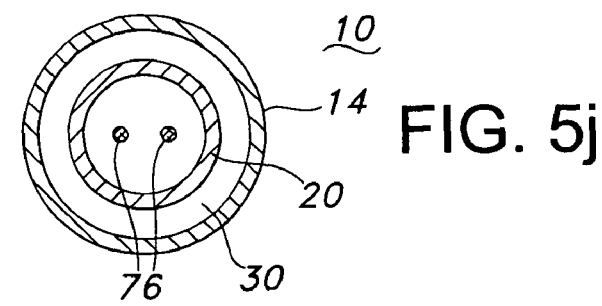
Figure 5K:
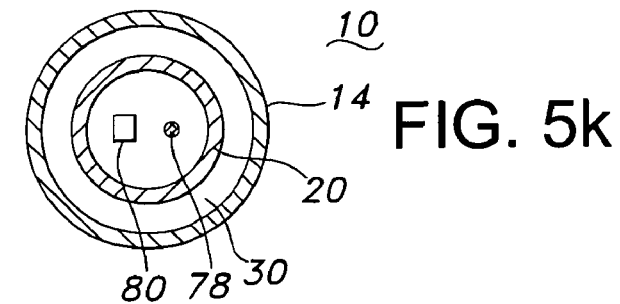

FIG. 5d represents the inner and outer tubular members 20 and 14 being utilized with multiple instruments 62 and 64, for example, a 2.2 mm scissors and a 2.2 mm. grasper, such that a single trocar assembly 10 may permit two or more instruments to be passed through the flow of fluid comprising the fluid wall 40, wherein the operating surgeon(s) may work each instrument simultaneously through a single trocar. FIG. 5e represents the inner and outer tubular members 20 and 14 utilized with an instrument 66 having a shaft of irregular cross-sectional shape. FIG. 5f represents the inner and outer tubular members 20 and 14 receiving a sharp tipped instrument 68 therethrough, such as for example, a pair of scissors. FIG. 5g represents the inner and outer tubular members 20 and 14 having a spring loaded instrument 70 (Nitinol/stainless steel or the like) that may for example, activate a mechanical/plastic seal. FIG. 5h represents a tissue specimen 72 being removed through the inner tubular member 20 without the need for mechanical disengagement/engagement of a mechanical seal. The inner channel 21 of the inner tubular member 20 it is to be noted, is self clearing of debris by virtue of the return fluid/gas "R" flowing therewithin. FIG. 5i represents the inner and outer tubular members 20 and 14 permitting the introduction of an irregularly shaped surgical material 74, such as a sponge or a prolene mesh for hernia repairs or the like. FIG. 5j represents the inner and outer tubular members 20 and 14 for sutures 76 to be externalized for knot tying and knot advancement in the surgical field. FIG. 5k represents the inner and outer tubular members 20 and 14 arranged to allow a suture 78 and an instrument 80 to be utilized concurrently.

Figure 6:
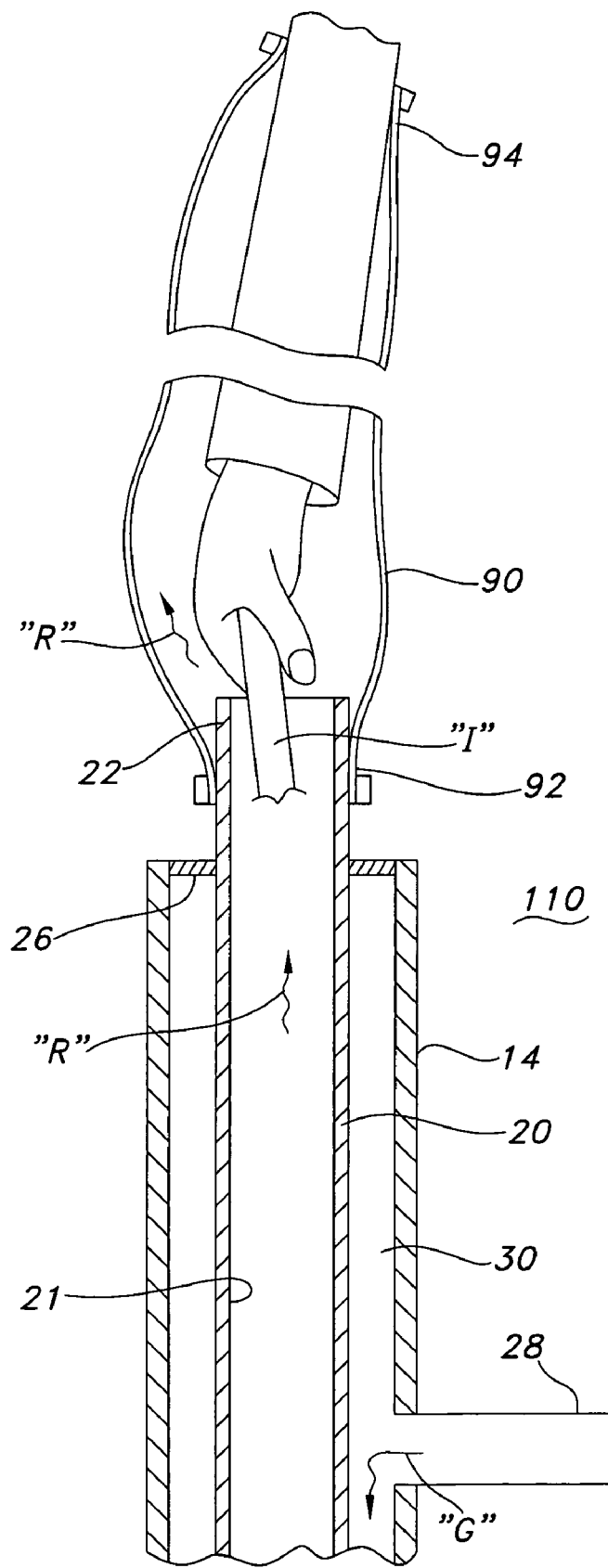
FIG. 6 represents a cross-sectional view of the trocar with a flexible, generally fluid tight sleeve attached to the upper or proximalmost end thereof for receipt of the surgeon's forearm, to permit generally fluid-tight manipulation of an instrument within the patient.

A yet further preferred embodiment of the present invention of the trocar assembly 10 relating to hand assisted laparoscopic surgery is represented in FIG. 6. As shown there, an expanded/expandable flexible sleeve extension 90 having a first end 92 arranged onto the proximal end 22 of the trocar assembly 10, the sleeve extension 90 having a second end 94 snugly arranged about the operating surgeon's forearm. An instrument "I" is shown as manipulable through the inner tubular member 20, providing a sealing to the returning fluid/gas "R". The surgeon thus having full tactile response to the manipulation of that instrument "I" through a universal seal (a wall of fluid/gas, related to the Coanda effect), while maintaining an equilibrium of pneumoperitoneum pressure of about 28 to 30 mm., without that instrument having any touching or interference by engagement with the walls or any hard seal mechanism of the trocar assembly common in the prior art.

Figure 7:
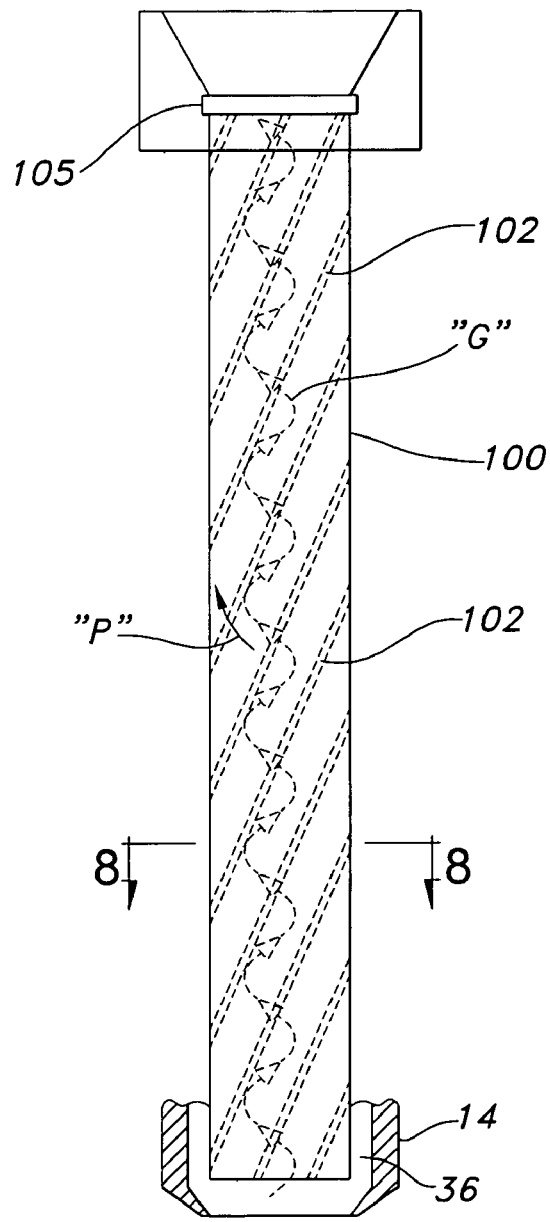
FIG. 7 is a side elevational view representing grooves in the inner tubular member with the separation of liquid and gas thereby.

FIG. 7 shows a further embodiment of the inner tubular member 100 having an arrangement of spiral lands and grooves 102 disposed on the inner surface thereof to cause the exhaust gas flow to rotate as it passes out through the trocar 100. This rotation causes liquid droplets and particulates "P" to separate out of the axial gas flow "G" due to centripetal forces. These droplets collect on the inner surface of the trocar 100. The general gas flow towards the proximal end of the trocar 100 will drive the collected matter towards the proximal end of the inner tube 100 to a collection annulus 104 at the proximalmost end of the trocar 100. A drain tube or egress port 105 may be arranged to permit this material to exit the working area to a collection reservoir or pad (not shown).

Figure 8:
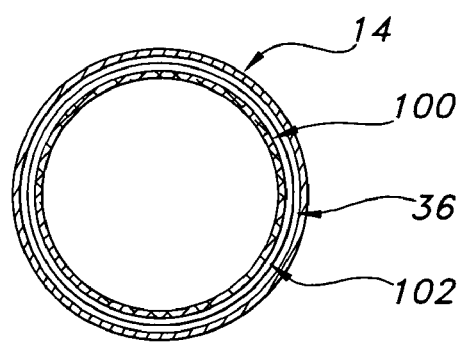
FIG. 8 is a view taken along the lines 8-8 of FIG. 7.
Figure 9:
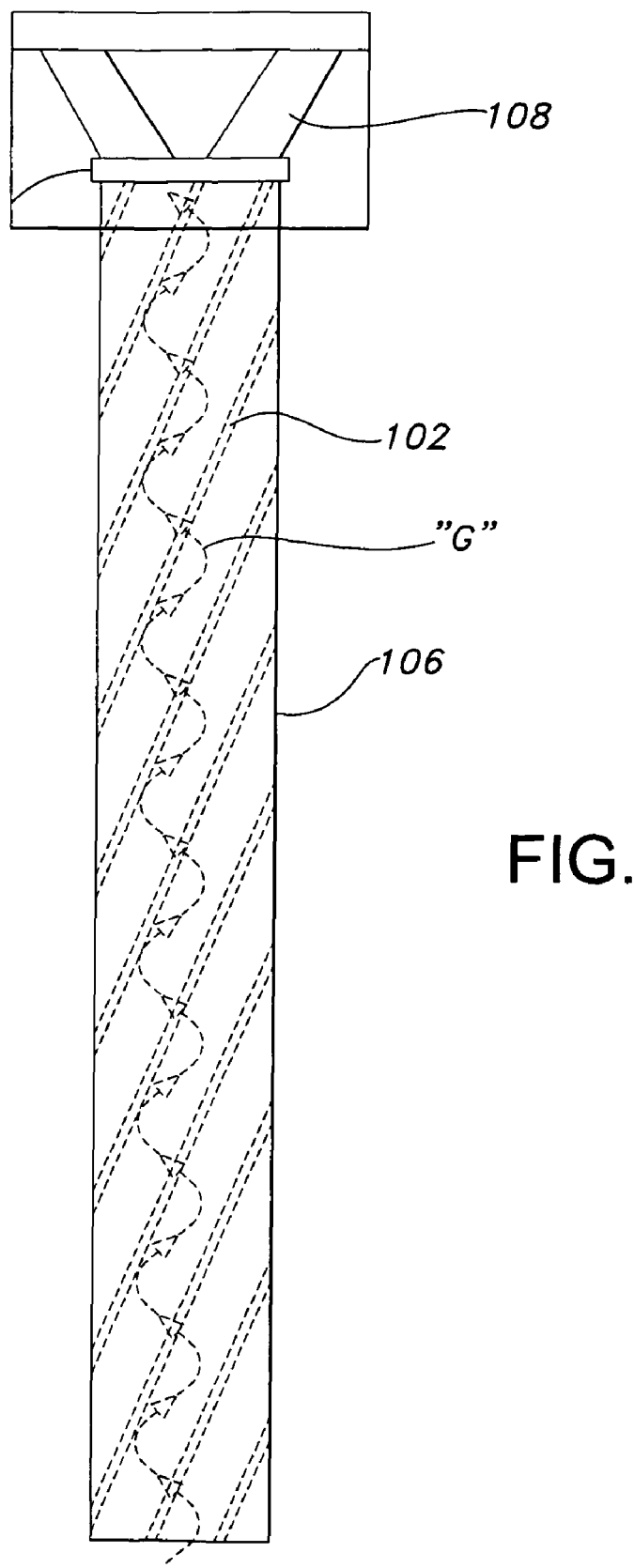
FIG. 9 is a side elevational view of the inner tubular member showing a duck-bill type valve arranged therein.

FIG. 8 is a cross-sectional view of the inner tubular member 100 with its internal grooves 102, and also showing the location of the annular nozzle segments 37, and the outer tubular member 14. FIG. 9 shows a representation of an inner tubular member/cannula 106 with a duckbill valve 108 arranged on/near the proximal end thereof. The duck bill valve 108 prevents splash of liquid and particular matter and undesired gas flow from exiting the proximal end of the inner tubular member 106.

We claim:

1. A trocar assembly for providing a pressurized insufflation fluid into a patient cavity and sealable access to said patient cavity by a surgical instrument, comprising:
    a) an inner tubular member having a proximal end portion and a distal end portion;
    b) an outer tubular member disposed about the inner tubular member, the outer tubular member having a proximal end portion and a distal end portion, the distal end portion of the inner tubular member and the distal end portion of the outer tubular member defining a trocar fluid seal nozzle arranged therebetween, wherein the trocar fluid seal nozzle provides a pressurized fluid seal for penetration by a surgical instrument during a surgical procedure upon the patient.

2. The trocar assembly as recited in claim 1, wherein the trocar fluid seal nozzle arrangement introduces a wall of fluid material delivered between the distal end portion of the inner tubular member and the distal end portion of the outer tubular member.

3. The trocar assembly as recited in claim 1, wherein the trocar fluid seal nozzle is of arcuate configuration to conform to said the inner and outer tubular members.

4. The trocar assembly as recited in claim 1, wherein the inner tubular member includes a fluid return channel for insufflation fluid returned from the patient.

5. The trocar assembly as recited in claim 1, wherein the inner tubular member has an inner surface with a spiral groove arrangement disposed thereon.

6. The trocar assembly as recited in claim 1, wherein the inner tubular member has a valve arrangement disposed across a proximal end portion thereof.

7. The trocar assembly as recited in claim 6, wherein the valve on the proximal end portion of the inner tubular member includes a duck bill valve.

8. The trocar assembly as recited in claim 1, wherein at least one of the inner and outer tubular members has a pressure sensor arranged with a fluid pressure source to control fluid introduction into the patient.

9. The trocar assembly as recited in claim 1, wherein the pressurized fluid seal defines a wall of pressurized air.

10. The trocar assembly as recited in claim 9, wherein the wall of pressurized air is generally conical in configuration.

11. The trocar assembly as recited in claim 1, including a regulatable pressurized source in communication with the outer tubular member.

12. The trocar assembly as recited in claim 1, wherein the trocar fluid seal nozzle is adjustable.

13. The trocar assembly as recited in claim 12, wherein the inner tubular member is rotatably adjustable with respect to the outer tubular member.

14. The trocar assembly as recited in claim 12, wherein the inner tubular member is longitudinally adjustable with respect to the outer tubular member.

15. The trocar assembly as recited in claim 1, wherein the inner tubular member and the outer tubular member have an annular space therebetween defining a plenum chamber for introduction of pressurized fluid from a pressurized fluid source in communication with the plenum chamber to a fluid discharge nozzle at the distal end portion of the trocar assembly to create a wall of pressurized fluid for sealing the trocar assembly.

16. The trocar assembly as recited in claim 1, including a flexible sleeve attached to the proximal end portion of the inner tubular member, wherein the sleeve is arranged for receipt of a surgeon's forearm during manipulation of a surgical instrument through the trocar assembly and within the patient.

17. An access device for use in a surgical procedure within a body cavity, comprising:
    a) an inner tubular member having opposed proximal and distal end portions;
    b) an outer tubular member having opposed proximal and distal end portions; and
    c) a nozzle operatively associated with the inner and outer tubular members for discharging pressurized fluid, wherein the nozzle is adapted and configured to develop a pressurized fluid seal flowing directly around a surgical instrument introduced into the body cavity through the access device, and wherein the pressurized fluid seal directly contacts a surgical instrument without any intervening structure therebetween.

18. An access device as recited in claim 17, wherein a pathway is defined between the inner and outer tubular members for directing pressurized fluid to the nozzle.

19. An access device as recited in claim 18, further including inlet means for receiving pressurized fluid from a fluid source, wherein the inlet means is in fluid communication with the pathway defined between the inner and outer tubular members.

20. An access device as recited in claim 17, wherein the nozzle is adapted and configured to introduce pressurized fluid into a body cavity.

21. An access device as recited in claim 17, further comprising a fluid return channel for accommodating the return of pressurized fluid from a body cavity.

22. An access device as recited in claim 17, wherein the nozzle is arranged in a circumferential manner relative to a longitudinal axis of the trocar.

23. An access device as recited in claim 22, wherein the nozzle is arranged in such a manner so as to direct pressurized fluid toward the longitudinal axis of the trocar.

24. An access device as recited in claim 22, wherein the nozzle is associated with the distal end portions of the inner and outer tubular members.

25. An access device as recited in claim 24, wherein the nozzle is formed at the distal end portions of the inner and outer tubular members.

26. An access device as recited in claim 17, wherein the nozzle includes an annular array of fluid directing jets.

* * * * *